US00PP24172P3

(12) United States Plant Patent
Olesen et al.

(10) Patent No.: US PP24,172 P3
(45) Date of Patent: Jan. 21, 2014

(54) ***CLEMATIS* PLANT NAMED 'EVIPO042'**

(50) Latin Name: *Clematis viticella*
Varietal Denomination: Evipo042

(75) Inventors: Mogens Nyegaard Olesen, Fredensborg (DK); Raymond J. Evison, St. Sampsons (GB)

(73) Assignee: Poulsen Roser A/S, Fredensburg (DK)

( * ) Notice: Subject to any disclaimer, the term of this patent is extended or adjusted under 35 U.S.C. 154(b) by 0 days.

(21) Appl. No.: 13/374,055

(22) Filed: Dec. 9, 2011

(65) Prior Publication Data

US 2012/0090060 P1 Apr. 12, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

(56) References Cited

PUBLICATIONS

GTITM UPOVROM Citation for 'Evipo042' as per QZ PBR 20100225; Feb. 3, 2010.*

* cited by examiner

*Primary Examiner* — Kent L Bell

(57) ABSTRACT

A new *Clematis* plant with a compact growth habit, profuse, purple flowers, and continuous summer flowering. The variety successfully propagates from softwood cuttings and is suitable for cultivation commercial glasshouse and nursery culture. This new and distinct variety has shown to be uniform and stable in the resulting generations from asexual propagation from vegetative cuttings.

3 Drawing Sheets

Botanical classification: Genus: *Clematis*. Species: *viticella*.

Variety denomination: 'Evipo042'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1995 and the resulting seeds were planted the following winter in a controlled environment in Guernsey, Channel Islands, United Kingdom. The new variety named 'Evipo042' originated as a single seedling from the stated cross.

The new *clematis* plant may be distinguished from its female seed parent primarily by growth habit. The female seed parent is less compact than the new variety.

The new *clematis* plant may be distinguished from its male pollen parent by flower color. The new variety is purple, while the male pollen parent is pink.

The objective of the hybridization of this *clematis* plant was to create a new and distinct variety for glasshouse and nursery culture with unique qualities such as:

1. Uniform and abundant purple flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo042' was selected by Mogens N. Olesen and Raymond J. Evison in their *clematis* development program in the Channel Islands, United Kingdom in 1996. Asexual reproduction of 'Evipo042' by means of vegetative cuttings and traditional layering was first performed by Mogens N. Olesen and Raymond J. Evison in the nursery during the summer of 1996. This initial and subsequent asexual propagations have demonstrated that the characteristics of 'Evipo042' are true to type and are transmitted from one generation to the next.

BRIEF DESCRIPTION OF THE DRAWING

The accompanying color illustration show as true as is reasonably possible to obtain in color photographs of this type.

DETAILED DESCRIPTION OF THE VARIETY

Figure 1:
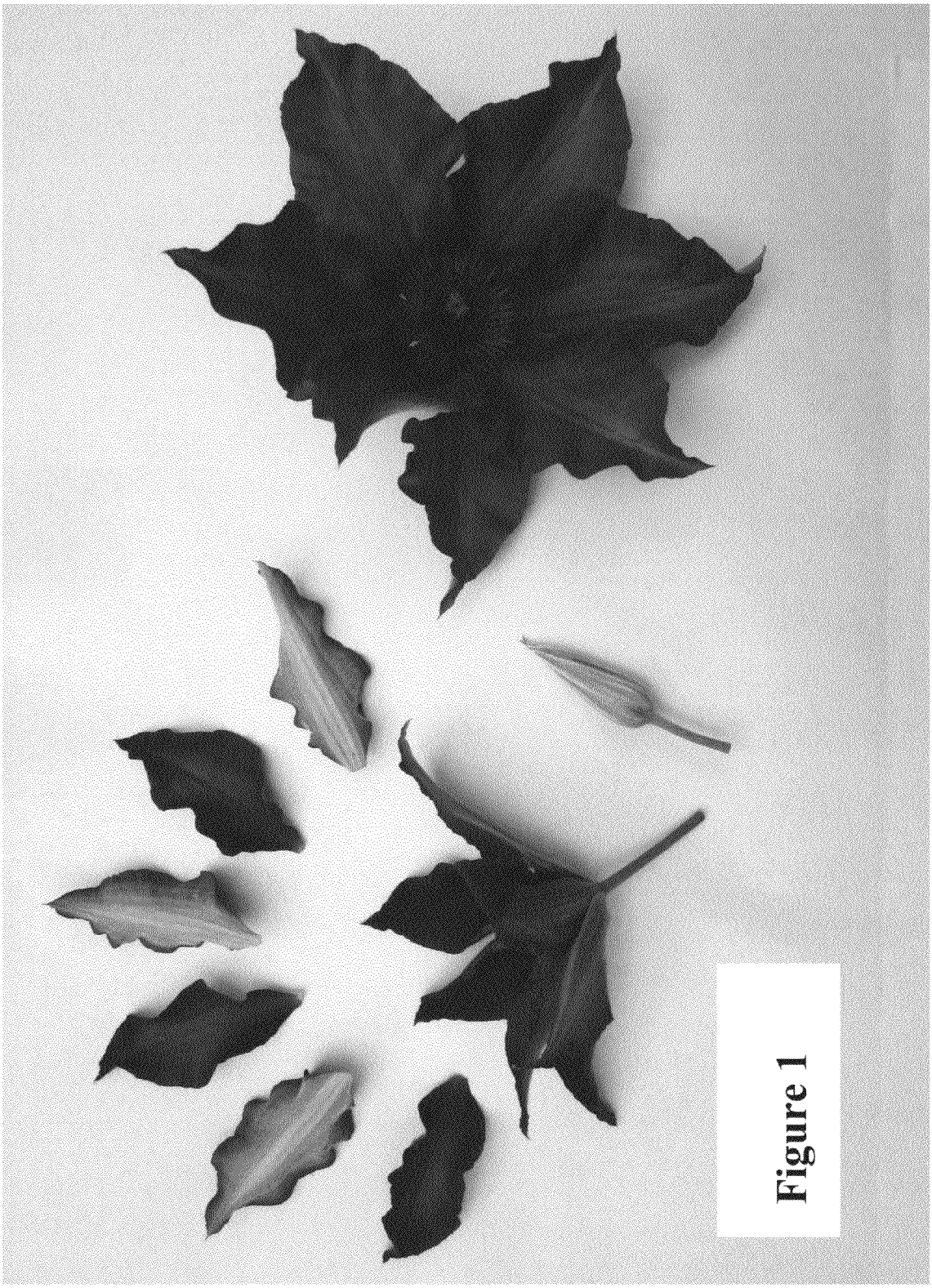
FIG. 1. Flower at various stages of opening, and tepals detached.
Figure 2:
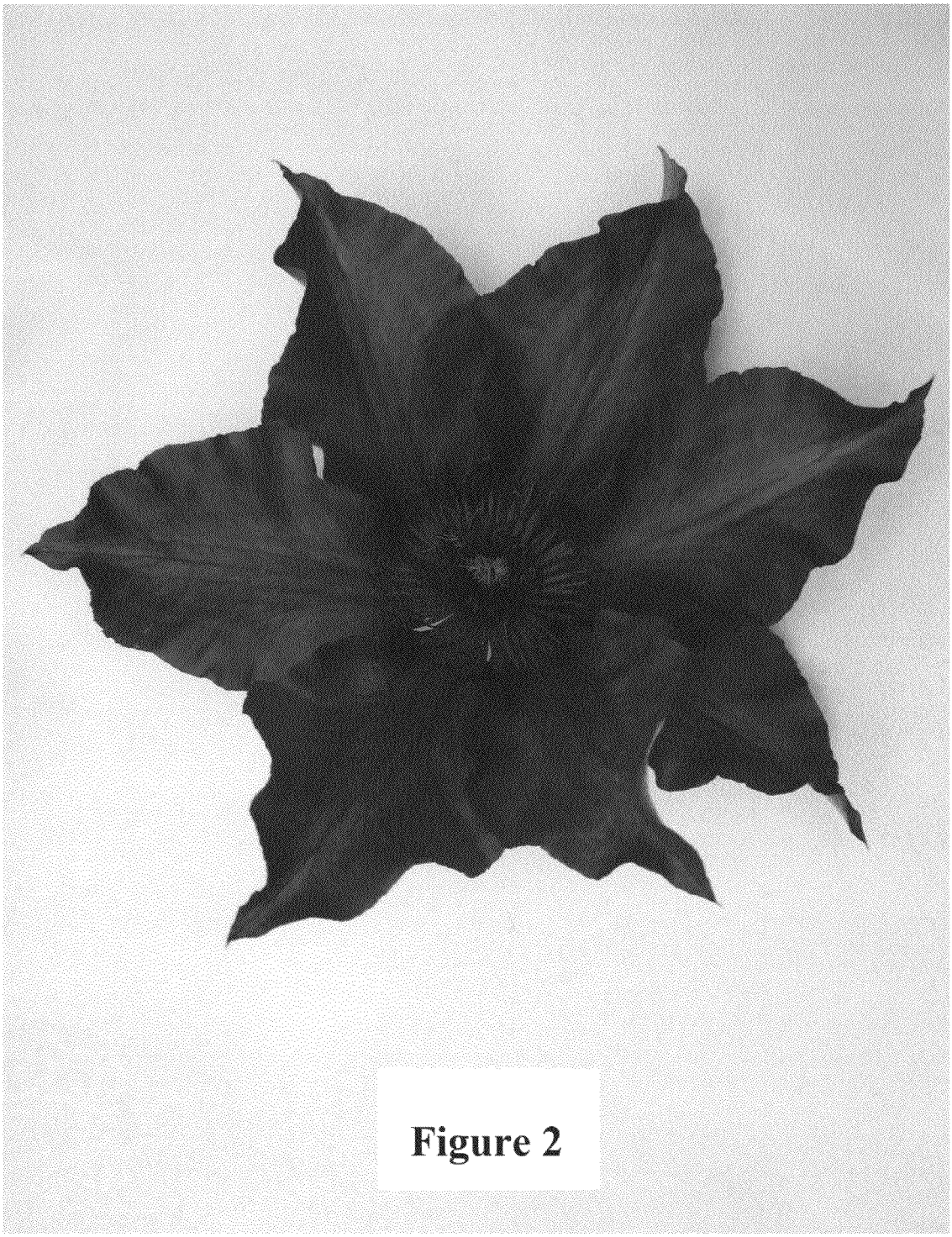
FIG. 2. Open flower.
Figure 3:
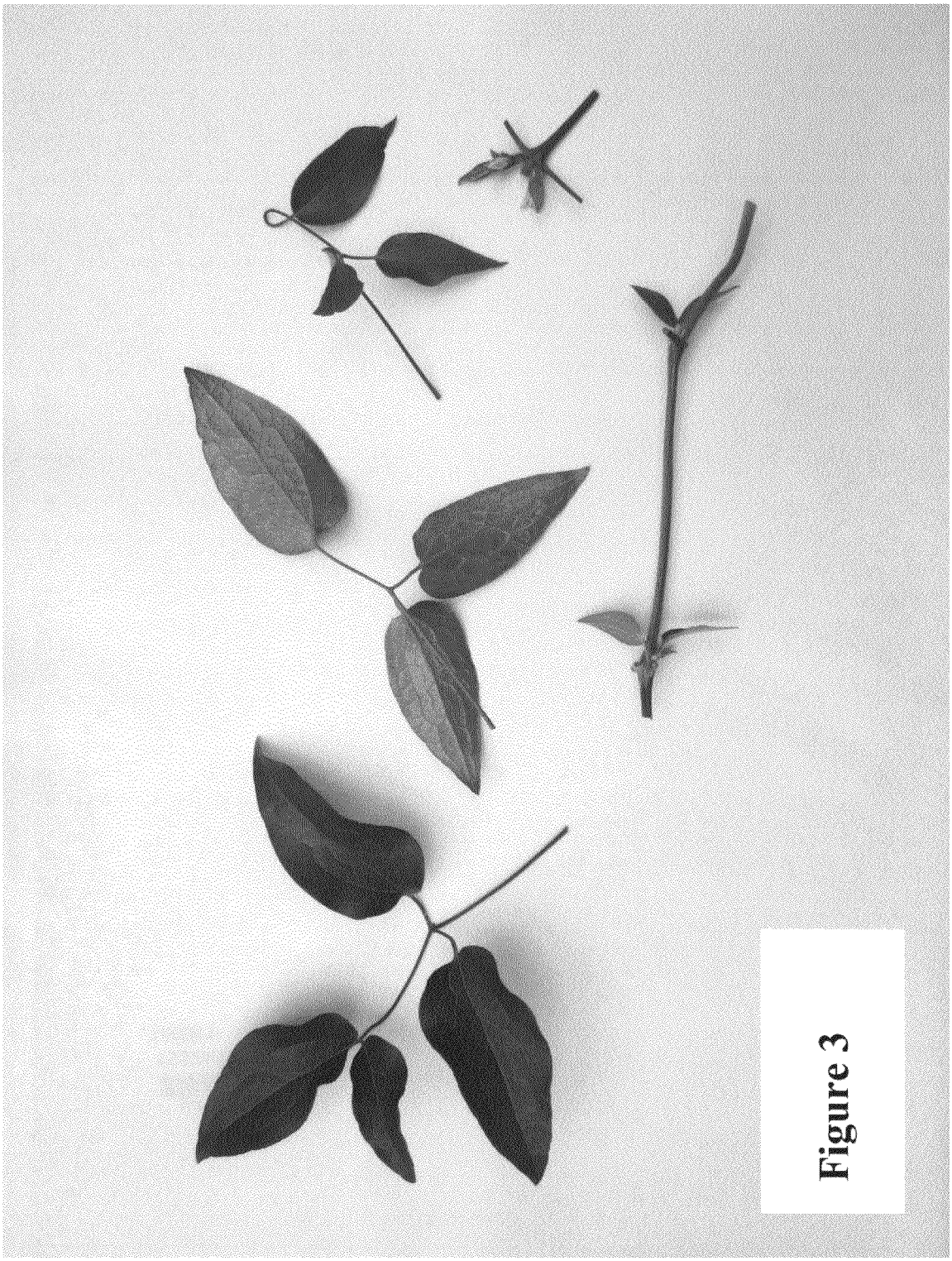
FIG. 3. Stems and leaves.

The following is a detailed description of 'Evipo042', as observed in its growth throughout the flowering period in open air container production in Yamhill County Oreg. Observed plants were cultivated for a period of 24 months in 1 gallon containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety Evipo024 described and illustrated in U.S. Plant Pat. No. 15,156 are compared to 'Evipo042' in Chart 1.

CHART 1

| | 'Evipo042' | Evipo024 |
|---|---|---|
| Flower diameter | 170 mm | 90 to 130 mm |
| Tepal upper surface, upon opening | Purple Group N79A with intonations of Purple Group N78A | RHS N79D of the Purple Color Group |
| Color of anthers | Violet Blue Group N92A | Yellow Group 2D with Red Purple Group 72A longitudinal bar |

FLOWER AND FLOWER BUD

Blooming habit: Continuous. The natural flowering period is generally from early May to September.

Flower bud:

*Size.*—Normally 40 mm in length. Bud diameter is 12 mm.

*Bud form.*—Elliptical with a broad base.

*Bud color.*—Yellow-Green Group 148C with intonations of Greyed-Purple Group 187A towards the apex.

*Texture.*—Very pubescent.

Pedicel:

*Surface.*—Smooth and very pubescent.

*Length.*—50 to 60 mm.

*Color.*—Yellow-Green Group 147C with intonations of Greyed-Purple Group N186C and Greyed-Purple Group 183A.

*Strength.*—Strong.

Receptacle:

*Surface texture.*—Very pubescent.

*Shape.*—Funnel.

*Size.*—2 mm (h)×5 mm (w).

*Color.*—Yellow-Green Group 147C with intonations of Greyed-Purple Group N186C and Greyed-Purple Group 183A.

Flower arrangement:

*Location on vine.*—New and old growth.

*Borne.*—Singly.

Flower bloom:

*Size.*—On average, flowers are 170 mm in diameter and 25 mm in depth.

*Profile.*—Open flowers are broad funnel when viewed from the side. The upper portion is flat, lower portion is convex.

*Fragrance.*—None.

*Lasting quality.*—Flowers normally remain 7 to 10 days on the plant. As a cut flower, flowers normally last 3 to 4 days.

Tepals:

*Tepal color.*—Upon opening, the upper surface is Purple Group N79A with intonations of Purple Group N78A. The lower surface is Purple Group 76A with Purple Group N79A at margins. There is a central bar the color of Greyed-Green Group 195B on the lower surface. After opening, the upper surface is Violet Group 83A at margins and Purple-Violet Group N80B at the mid-section. The lower surface is Purple Group 76A with Purple Group N79A at margins. There is a central bar the color of Greyed-Green Group 195B on the lower surface.

*Quantity.*—Normally 7 tepals.

*Size.*—85 mm in length by 45 mm wide.

*Shape.*—Individual tepal shape is elliptical. The tepal apex is acute. The tepal base acute.

*Apex recurvature.*—Slightly recurved.

*Tepal cross section.*—Slightly reflexed.

*Margins.*—Entire. Moderate undulations of margin observed.

*Persistence.*—Tepals drop off cleanly.

Reproductive organs:

*Arrangement.*—Moderately open.

*Pollen.*—None observed.

*Anthers.*—Size: 5 mm in length. Color: Violet Blue Group N92A. Quantity: 75 on average.

*Filaments.*—Color: Red-Purple Group N74C. Length: 7 mm.

*Pistils.*—Quantity: 65 on average.

*Stigmas.*—Inferior in location relative to the length of the filaments and the height of the anthers.

*Styles.*—Color: White Group 155B. Length: 10 mm.

Seed head characteristics: None observed.

PLANT

Plant form: Climbing.

Plant growth: Moderately vigorous and very compact.

Size: Seasons growth attains 80 cm to 1 meter in height. Average spread is 45 cm.

Hardiness: Trials to date show the variety hardy in USDA Zones 6.

Stems:

*Color.*—Juvenile stems are generally Yellow-Green Group 146B. Other intonations observed are strong intonations of Greyed-Orange Group 177A. Mature stems are Greyed-Red Group 178A.

*Internodes.*—7 to 10 cm between nodes.

*Length.*—Normally 30 cm from the base of the plant to the flowering portion of the stem.

*Diameter.*—Normally 4 mm. Surface: Mature stems are smooth with ribs parallel to the stem.

Plant foliage:

*Leaf characteristics.*—Deciduous.

*Arrangement.*—3 to 5 leaflets.

*Leaf size.*—Compound leaves are normally 180 mm (l)× 180 mm (w). Leaflets are normally 85 mm (l)× 40 mm (w).

*Abundance.*—Generally, there are 2 leaves per 10 cm of stem.

*Leaf color.*—The upper surfaces of mature leaflets are Yellow-Green Group 147A while the lower surfaces are Yellow-Green Group 147C. Upper surfaces of juvenile leaflets are are Yellow-Green Group 146B while the lower surfaces are Yellow-Green Group 146C.

*Stipules.*—Absent.

*Petioles.*—Size: Normally 55 to 65 mm in length by 1.5 mm diameter. Texture: Smooth and pubescent. Color: Yellow-Green Group 146B with strong intonations of Brown Group 200B.

*Petioloule.*—Size: Normally 30 mm in length by 1.5 mm diameter. Texture: Smooth and pubescent. Color: Yellow-Green Group 146B with strong intonations of Brown Group 200B.

*Leaflet shape.*—Generally elliptic. The base is oblique and rounded. The apex is acute.

*Margin.*—Entire.

*Surface.*—The upper side is smooth. The lower side is smooth.

*Thickness.*—Moderate.

*Glossiness.*—Moderately glossy.

Disease resistance: Subject to any disease that normally attacks the species. However the variety is more tolerant to *clematis* wilt than some *clematis*.

We claim:

1. A new and distinct variety of *clematis* plant named 'Evipo042', substantially as described and illustrated, due to its abundant purple flowers with good keepability, attractive foliage, compact growth, suitability for production from softwood cuttings in pots, durable flowers and foliage, which make the variety suitable for distribution in the floral industry.

* * * * *